(12) United States Patent
Godden

(10) Patent No.: US 8,744,593 B2
(45) Date of Patent: Jun. 3, 2014

(54) GEL FORMED BATTERY

(75) Inventor: Glenn Godden, Edmonds, WA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/392,424

(22) PCT Filed: Apr. 8, 2011

(86) PCT No.: PCT/US2011/031780
§ 371 (c)(1),
(2), (4) Date: Feb. 24, 2012

(87) PCT Pub. No.: WO2012/138351
PCT Pub. Date: Oct. 11, 2012

(65) Prior Publication Data
US 2012/0259391 A1    Oct. 11, 2012

(51) Int. Cl.
*A61N 1/00* (2006.01)

(52) U.S. Cl.
USPC .................................................. 607/75

(58) Field of Classification Search
USPC .................................................. 607/75
See application file for complete search history.

(56) References Cited

U.S. PATENT DOCUMENTS

| | | |
|---|---|---|
| 4,055,291 A | 10/1977 | Peters |
| 4,461,403 A | 7/1984 | Prahs |
| 4,746,221 A | 5/1988 | Okumura et al. |
| 4,808,496 A | 2/1989 | Hope et al. |
| 5,020,694 A | 6/1991 | Pettengill |
| 5,569,368 A | 10/1996 | Larsky et al. |
| 6,230,052 B1 | 5/2001 | Wolff et al. |
| 6,383,536 B1 | 5/2002 | Palmer et al. |
| 6,395,428 B1 | 5/2002 | Kezuka |
| 6,416,800 B1 | 7/2002 | Weber et al. |
| 7,008,722 B2 | 3/2006 | Huang |
| 7,378,450 B2 | 5/2008 | Erkey et al. |
| 7,476,221 B2 | 1/2009 | Sun et al. |
| 7,476,222 B2 | 1/2009 | Sun et al. |
| 7,477,939 B2 | 1/2009 | Sun et al. |

(Continued)

FOREIGN PATENT DOCUMENTS

| | | |
|---|---|---|
| AU | 1305188 A | 9/1989 |
| AU | 02358277 A1 | 7/2003 |

(Continued)

OTHER PUBLICATIONS

International Search Report and Written Opinion for PCT/US2012/032753 issued Jul. 19, 2012, 13 pages.

(Continued)

Primary Examiner — Christopher D Koharski
Assistant Examiner — Nadia Ahmad
(74) Attorney, Agent, or Firm — Foley & Lardner LLP

(57) ABSTRACT

An apparatus includes a cathode chamber configured to store a gel cathode and an anode chamber configured to store a gel anode. A cathode dispensing channel is in fluid communication with the cathode chamber and allows at least a portion of the gel cathode to be dispensed. An anode dispensing channel is in fluid communication with the anode chamber and allows at least a portion of the gel anode to be dispensed. A portion of the gel cathode and a portion of the gel anode come into contact upon being dispensed to form an active battery that can be used to generate an electrical current.

26 Claims, 8 Drawing Sheets

(56) References Cited

U.S. PATENT DOCUMENTS

| | | | |
|---|---|---|---|
| 7,477,941 B2 | 1/2009 | Sun et al. | |
| 7,477,947 B2 * | 1/2009 | Pines et al. | 607/134 |
| 7,632,533 B2 | 12/2009 | Fotland et al. | |
| 8,007,935 B2 | 8/2011 | He et al. | |
| 2002/0029973 A1 | 3/2002 | Maydan | |
| 2003/0102874 A1 | 6/2003 | Lane et al. | |
| 2004/0070371 A1 | 4/2004 | Chern et al. | |
| 2004/0071866 A1 | 4/2004 | Park et al. | |
| 2004/0141908 A1 | 7/2004 | Hara et al. | |
| 2004/0164096 A1 | 8/2004 | Engel et al. | |
| 2005/0013862 A1 | 1/2005 | Tobyn et al. | |
| 2005/0053830 A1 | 3/2005 | Akashi et al. | |
| 2005/0089548 A1 | 4/2005 | Virgalitto et al. | |
| 2005/0233208 A1 | 10/2005 | Tang | |
| 2006/0261823 A1 | 11/2006 | Parker | |
| 2007/0059595 A1 | 3/2007 | Endo et al. | |
| 2007/0060862 A1 | 3/2007 | Sun et al. | |
| 2007/0111104 A1 | 5/2007 | Shibuya | |
| 2007/0123772 A1 | 5/2007 | Euliano et al. | |
| 2007/0142222 A1 | 6/2007 | Erkey et al. | |
| 2007/0236867 A1 | 10/2007 | Hossick-Schott et al. | |
| 2007/0282387 A1 | 12/2007 | Starkebaum | |
| 2007/0286929 A1 | 12/2007 | Andersen | |
| 2008/0009775 A1 | 1/2008 | Murison | |
| 2008/0050490 A1 | 2/2008 | Stalder et al. | |
| 2008/0171266 A1 | 7/2008 | Kato et al. | |
| 2008/0284599 A1 | 11/2008 | Zdeblick et al. | |
| 2009/0010998 A1 | 1/2009 | Marchitto et al. | |
| 2009/0136834 A1 | 5/2009 | Coowar et al. | |
| 2009/0270788 A1 | 10/2009 | Marenus et al. | |
| 2009/0286153 A1 | 11/2009 | He et al. | |
| 2009/0314336 A1 | 12/2009 | Nakatani et al. | |
| 2010/0055570 A1 | 3/2010 | Rodriguez | |
| 2010/0057147 A1 | 3/2010 | Fassih et al. | |
| 2010/0082088 A1 | 4/2010 | Fassih et al. | |
| 2010/0209515 A1 | 8/2010 | Chantalat et al. | |
| 2010/0239616 A1 * | 9/2010 | Hafezi et al. | 424/400 |
| 2010/0298668 A1 | 11/2010 | Hafezi et al. | |
| 2011/0052764 A1 | 3/2011 | Bulgin | |
| 2011/0065983 A1 | 3/2011 | Hafezi et al. | |
| 2011/0184482 A1 | 7/2011 | Eberman et al. | |
| 2012/0021014 A1 | 1/2012 | Chantalat et al. | |
| 2012/0276443 A1 | 11/2012 | Hatta et al. | |

FOREIGN PATENT DOCUMENTS

| | | |
|---|---|---|
| AU | 2008281632 A1 | 2/2009 |
| AU | 2009281876 A1 | 2/2010 |
| CA | 2734251 A1 | 2/2010 |
| CN | 1617765 A | 5/2005 |
| CN | 101174681 B | 5/2010 |
| CN | 101227001 B | 9/2011 |
| CN | 102176862 A | 9/2011 |
| EP | 1494807 A2 | 1/2005 |
| EP | 2173323 A2 | 4/2010 |
| EP | 1959023 B1 | 5/2010 |
| EP | 2313003 A2 | 4/2011 |
| EP | 2057703 B1 | 11/2013 |
| FI | 20065423 A | 12/2007 |
| GB | 2451503 A | 2/2009 |
| GB | 2455184 A | 6/2009 |
| JP | 2004134351 A | 4/2004 |
| JP | 2005209819 | 8/2005 |
| JP | 2006504508 A | 2/2006 |
| JP | 2007323878 | 12/2007 |
| JP | 4199811 B2 | 12/2008 |
| JP | 2012500055 A | 1/2012 |
| KR | 20040032421 A | 4/2004 |
| KR | 20110041563 A | 4/2011 |
| MX | PA04006324 A | 3/2005 |
| TW | 200930415 A | 7/2009 |
| WO | 03057367 A2 | 7/2003 |
| WO | WO 2005/004981 A2 | 1/2005 |
| WO | WO 2005/004983 A2 | 1/2005 |
| WO | 2005045977 A2 | 5/2005 |
| WO | WO 2007/147942 A1 | 12/2007 |
| WO | 2008052394 A1 | 5/2008 |
| WO | WO 2008/052136 A2 | 5/2008 |
| WO | 2009016350 A3 | 2/2009 |
| WO | WO 2009/016350 A2 | 2/2009 |
| WO | WO 2009/045720 A1 | 4/2009 |
| WO | 2010019778 A3 | 2/2010 |
| WO | WO 2010/111511 A2 | 9/2010 |
| WO | WO 2012/012509 A1 | 1/2012 |
| WO | 2012138352 A1 | 10/2012 |
| WO | 2012138354 A1 | 10/2012 |
| WO | 2012138361 A1 | 10/2012 |
| WO | 2012139100 A1 | 10/2012 |
| WO | 2012139107 A1 | 10/2012 |
| WO | 2012139109 A1 | 10/2012 |

OTHER PUBLICATIONS

International Search Report and Written Opinion for PCT/US2012/032731 issued Jun. 22, 2012, 13 pages.

International Search Report and Written Opinion for PCT/US2012/032757 issued May 31, 2012, 11 pages.

International Search Report and Written Opinion for PCT Applicatgion No. PCT/US2011/031791, issued Jul. 7, 2011.

International Search Report and Written Opinion for PCT Application No. PCT/US2011/031780, issued Sep. 15, 2011.

International Search Report and Written Opinion for PCT Application No. PCT/US2011/031783, issued Aug. 17, 2011.

International Search Report and Written Opinion for PCT Application No. PCT/US2011/039281, issued Sep. 22, 2011.

Kendrick, Mandy, "Tasting the Light: Device Lets the Blind "See" with Their Tongues," Scientific American, Aug. 13, 2009.

Ramsewak et al., "Bioactive N-Isobutylamides from the Flower Buds of *Spilanthes acmella*," Phytochemistry, 51 (1999) 729-732.

Benwick, Bonnie S., "Like a Taste That Tingles? Then This Bud's for You," The Washington Post, Oct. 3, 2007.

"Solid-State Batteries the Power of the Press," The Economist, Jan. 27, 2011.

"From the Store Shelf to Home (and Beyond)," Ecoupled, Jan. 7, 2011, http://ecoupled.com/ces/from-the-store-shelf-to-home-and-beyond/.

Cass, Stephen, "Battery Storage Could Get a Huge Boost from Seaweed," Technology Review, Sep. 8, 2011.

Office Action for U.S. Appl. No. 13/260,446 issued Jun. 7, 2013.

Final Office Action in U.S. Appl. No. 13/260,446 dtd Oct. 9, 2013.

International Preliminary Report on Patentability in Intl. Appln. No. PCT/US2011/031780 dtd Oct. 17, 2013.

International Preliminary Report on Patentability in Intl. Appin. No. PCT/US2011/031791 dtd Oct. 17, 2013.

Notice of Allowance in U.S. Appl. No. 13/260,446 dtd Nov. 20, 2013 (14 pages).

"*Acmella oleracea*," Wikipedia, accessed at http://web.archive.org/web/20100801072959/http://en.wikipedia.org/wiki/Acmella_oleracea, last modified on Jul. 14, 2010, pp. 1-3.

"Battery (electricity)," Wikipedia, accessed at http://web.archive.org/web/20100830123459/http://en.wikipedia.org/wiki/Battery_(electricity), Aug. 28, 2010, pp. 1-14.

"Edible Computer Chips," Nanotechnology, Skinny Science, accessed at http://web.archive.org/web/20110310140822/ http://www.ediblecomputerchips.com/, Jan. 2009, pp. 1-8.

"Electrochemical Cell," Wikipedia, accessed at http://web.archive.org/web/20100219112124/http://en.wikipedia.org/wiki/Electrochemical_cell, accessed on Nov. 21, 2013, pp. 1-3.

"Pop Rocks," Wikipedia, accessed at http://web.archive.org/web/20110304100621/http://en.wikipedia.org/wiki/ Pop_Rocks, last modified on Feb. 28, 2011, pp. 1-3.

Brinn, D., "Israeli project develops novel solution to dry mouth," accessed at http://www.israel21c.org/health/israeli-project-develops-novel-solution-to-dry-mouth, Feb. 27, 2005, pp. 1-3.

(56) References Cited

OTHER PUBLICATIONS

Just, N. et al., "Bold responses to trigeminal nerve stimulation," Magnetic Resonance Imaging, vol. 28, pp. 1143-1151 (2010).
Lawless, H.T. et al., "Metallic Taste from Electrical and Chemical Stimulation," Chemical Senses, vol. 30, No. 3, pp. 185-194 (2005).
Stevens, D.A. et al., "A Direct Comparison of the Taste of Electrical and Chemical Stimuli," Chemical Senses, vol. 33, pp. 405-413 (2008).
Notice of Allowance in U.S. Appl. No. 13/260,446 dtd Jan. 17, 2014 (12 pages).

* cited by examiner

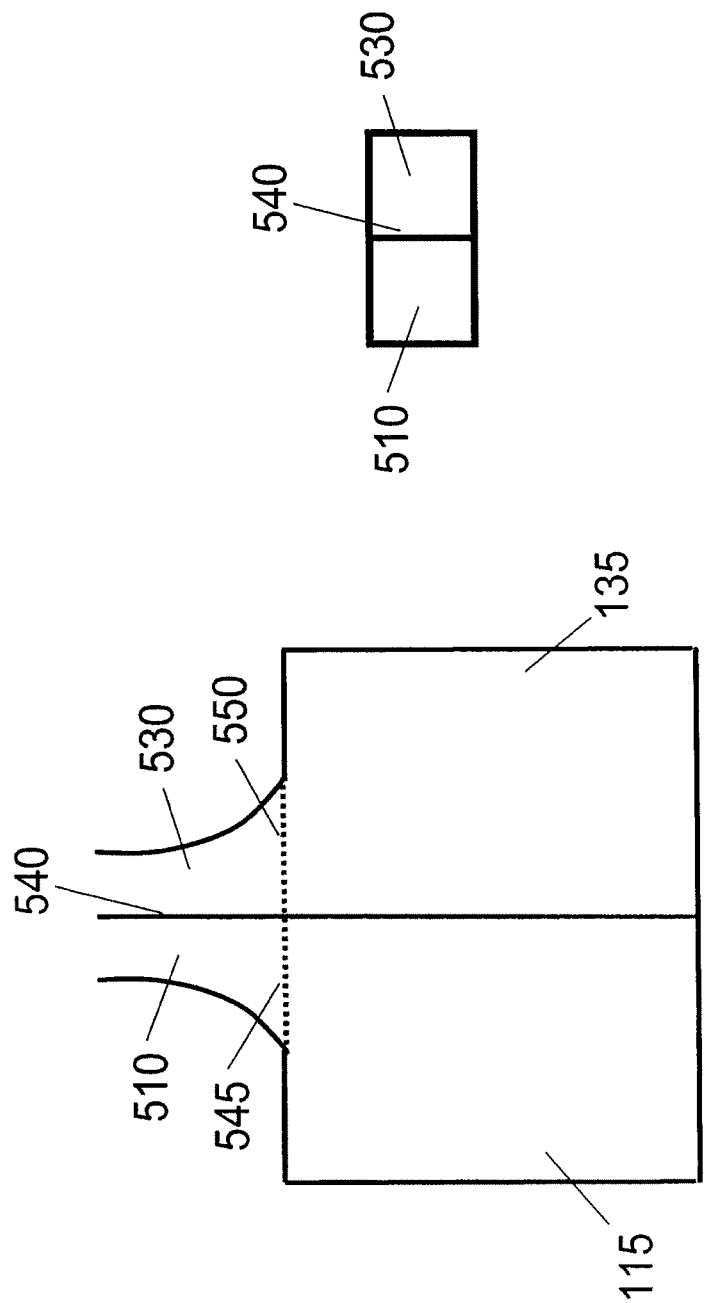

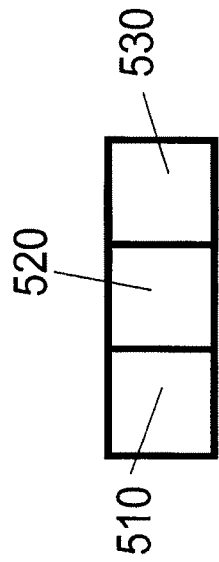
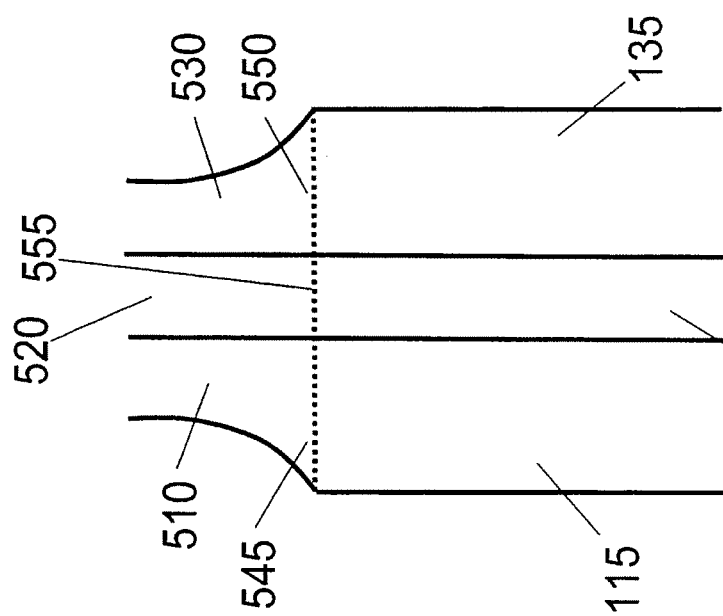
FIG. 6B
FIG. 6A

GEL FORMED BATTERY

CROSS-REFERENCE TO RELATED APPLICATIONS

This application is a U.S. national stage application claiming the benefit of International Application No. PCT/US2011/031780, filed on Apr. 8, 2011, the entire disclosure of which is incorporated by reference herein.

BACKGROUND

The following description is provided to assist the understanding of the reader. None of the information provided or references cited is admitted to be prior art.

A battery is an electro-chemical device that converts chemical energy into electrical energy. A battery generally includes an anode and a cathode, which are connected by an electrolyte. The electrolyte can be a wet electrolyte or a dry electrolyte that is activated by moisture. When the battery is in operation, a redox reaction occurs. During the redox reaction, reduction occurs to cations at the cathode and oxidization occurs to anions at the anode. The battery has a terminal voltage, which is measured as the difference of voltage between the anode and cathode.

SUMMARY

An illustrative apparatus includes a cathode chamber to store a gel cathode and an anode chamber to store a gel anode. A cathode dispensing channel is in fluid communication with the cathode chamber to dispense at least a portion of the gel cathode. An anode dispensing channel is in fluid communication with the anode chamber to dispense at least a portion of the gel anode. At least a portion of the gel anode and gel cathode come into contact upon exiting the cathode dispensing channel and the anode dispensing channel to form an active battery that generates an electrical current.

In one embodiment the gel anode includes a food grade gel anode and the gel cathode includes a food grade gel cathode. In one embodiment, the food grade gel anode is composed of copper, carbon, manganese dioxide, or iron. In another embodiment, the food grade gel cathode includes zinc or nickel. In yet another embodiment, at least one of the food grade gel anode and the food grade gel cathode includes a vitamin that is administered via the active battery.

In another embodiment, the apparatus includes a combination chamber that is in fluid communication with the cathode dispensing channel, the anode dispensing channel, and an external environment. The active battery is formed in the combination chamber.

In another embodiment, the cathode dispensing channel and the anode dispensing channel are in fluid communication with an external environment and the active battery is formed in the external environment.

In another embodiment, at least one of the gel anode and the gel cathode includes an electrolyte. In one embodiment, the electrolyte is one of a phosphoric acid, ascorbic acid, or salt.

In yet another embodiment, the apparatus includes an actuator that causes at least a portion of the gel cathode to enter the cathode dispensing channel and at least a portion of the gel anode to enter the anode dispensing channel.

In still another embodiment, the apparatus includes an electrolyte chamber to store a gel electrolyte. An electrolyte dispensing channel is in fluid communication with the electrolyte chamber and dispenses at least a portion of the gel electrolyte. A portion of the gel electrolyte comes into contact with at least the portion of the gel cathode and at least the portion of the gel anode to form the active battery.

In one embodiment, the active battery increases production of saliva. In another embodiment, the electrical current increases secretion of saliva.

In another embodiment, the gel anode includes cosmetic grade aluminum and the gel cathode includes cosmetic grade carbon. In one embodiment, the gel anode further comprises an electrolyte. In another embodiment, the active battery reduces perspiration. In yet another embodiment, the gel anode and/or the gel cathode includes a fragrance. In another embodiment, the gel anode and/or the gel cathode includes an antibacterial agent. In other embodiments, the active battery can be a facial mask, tooth paste, mouthwash gel, a teeth whitener, cleaner, shampoo, or hair dye. In some embodiments, the gel anode and/or the gel cathode includes a mint flavor. In another embodiment, the electrical current enhances application of a hair dye.

In other embodiments, the electrical current can reduce flora within a mouth, combat gum disease, enhance absorption of a drug, combat acne, stimulate a muscle, or provide sexual stimulation. In one embodiment, the active battery can be inserted into a vagina.

In another embodiment, the apparatus includes a separator that separates the cathode dispensing channel from the anode dispensing channel. In another embodiment, the cathode chamber and the anode chamber are formed from a non-conductive material.

In another embodiment, the apparatus includes a lotion chamber to store a lotion and that is in fluid communication with the anode dispensing channel and the cathode dispensing channel. In another embodiment, the gel anode and/or the gel cathode includes a lotion. In yet another embodiment, the apparatus includes an anode manifold in fluid communication with the anode dispensing channel that dispenses a plurality of portions of the gel anode. In this embodiment, the apparatus also includes a cathode manifold in fluid communication with the cathode dispensing channel to dispense a plurality of gel cathode portions. The plurality of gel anode portions and the plurality of gel cathode portions are interleaved to form a plurality of active batteries in series or parallel with one another.

In an illustrative process, a portion of a gel cathode is released from a cathode chamber and a portion of a gel anode is released from an anode chamber. At least the portion of the gel cathode contacts at least the portion of the gel anode to form an active battery that generates an electrical current. In another embodiment, the active battery is administered in a mouth of a subject to treat or prevent dry mouth.

In another illustrative apparatus, the apparatus includes means for storing a gel cathode, means for storing a gel anode, and means for causing at least a portion of the gel cathode to contact at least a portion of the gel anode to form an active battery that generates an electrical current.

In yet another illustrative embodiment, a pill includes a gel anode chamber to store a gel anode and a gel cathode chamber to store a gel cathode where the gel anode is separated from the gel cathode. The pill allows a portion of the gel anode and a portion of the gel cathode to come into contact to form an active battery that generates an electrical current.

In another illustrative embodiment, the apparatus includes a cathode chamber to store a gel cathode and an anode chamber to store a gel anode. The apparatus also includes a receptacle that houses the cathode chamber and the anode chamber, and that can be opened to bring at least a portion of the anode and the gel cathode into contact upon exiting the receptacle to form an active battery that generates an electrical current.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 5A illustrates a cathode chamber and an anode chamber in accordance with an illustrative embodiment.

FIG. 5B illustrates a front plan view of an anode dispensing channel and a cathode dispensing channel in accordance with an illustrative embodiment.

FIG. 6A illustrates a cathode chamber, an electrolyte chamber, and an anode chamber in accordance with an illustrative embodiment.

FIG. 6B illustrates a front plan view of an anode dispensing channel, an electrolyte dispensing channel, and a cathode dispensing channel in accordance with an illustrative embodiment.

DETAILED DESCRIPTION

Figure 1:
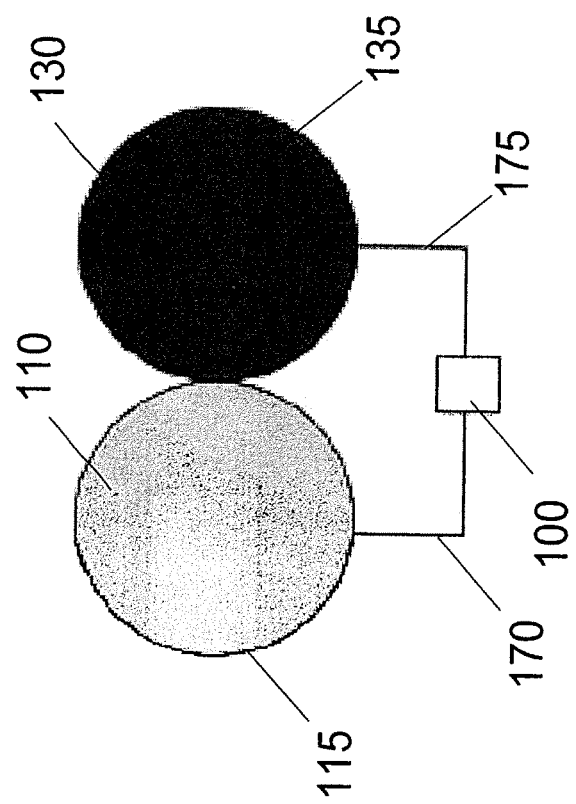
FIG. 1 illustrates a cathode chamber and an anode chamber in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Described herein are illustrative methods and apparatuses relating to a gel battery that is configured to deliver an electrical current. Non-limiting uses of the battery may include incorporation of the battery into an edible product, using the battery topically on humans, animals, plants, etc., to treat a condition, stimulate a muscle, reduce sweat, provide sexual pleasure, etc., using the battery to increase saliva production, using the battery to treat dry mouth or canker sores, using the battery as a breath freshener, using the battery as an antiseptic, using the battery to help deliver a vitamin or drug, using the battery to enhance a cleaning agent, using the battery as a lotion, etc. In one illustrative embodiment, components of the battery can include gel anodes, gel cathodes, and gel electrolytes. The components may be composed of food grade materials that are safe for human consumption. Non-limiting examples of food-grade anodes include copper, carbon, manganese dioxide, and iron. The food-grade cathode may be, but is not limited to, zinc or nickel. Non-limiting examples of a food-grade electrolyte include phosphoric acid, ascorbic acid, and salt. A gel battery can be activated by connecting the gel anode and the gel cathode in the presence of a gel electrolyte. In one embodiment, the gel electrolyte may be incorporated into one or both of the gel anode and the gel cathode. Upon activation, an electrical current can produce a noticeable sensation. For example, an edible gel battery can generate a current that may be felt, for example, in a mouth, gums, lips, stomach, etc.

The voltage of an illustrative battery may be increased or decreased in various ways. One such example is by using multiple batteries combined in series. For example, a second gel battery may be configured to be in series with a first gel battery. One or more additional batteries may similarly be connected in series with the first and second batteries to generate additional electrical voltage. Alternatively, multiple batteries can be combined in parallel with one another to increase current in a circuit.

It will be understood that the above embodiments and configurations are given as illustrative examples only and that other configurations of the battery will be apparent to those of skill in the art in light of the present disclosure. Additional details and embodiments are described with reference to the figures. FIG. 1 illustrates a cathode chamber 135 and an anode chamber 115 for forming a gel battery 100 in accordance with an illustrative embodiment. In one embodiment, the anode chamber 115 and the cathode chamber 135 can be incorporated into a dispenser for dispensing products such as, but not limited to, deodorants, toothpaste, shampoo, liquid soap, lotions, cleaners, etc. In other embodiments, the chambers 115 and 135 can be incorporated into a pill or into food products such as, but not limited to, gum, a jelly bean, candy, etc.

The cathode chamber 135 can store a gel cathode 130. Likewise, the anode chamber 115 can store a gel anode 110. The gel cathode 130 and/or the gel anode 110 can be made of various types of gels such as, but not limited to, aquagel, colloidal gel, hyrdogel, etc. In one embodiment, the gel cathode 130 can be made by adding a cathode such as, but not limited to, zinc or nickel, to a gel. Similarly, a gel anode can be made by adding to a gel an anode such as, but not limited to, copper, carbon, manganese dioxide, or iron. The anode or cathode can be incorporated in the gel by stirring or using a homogenizer. In one embodiment, the volume concentration of the anode and cathode is about 0.25. Other concentrations can also be used such as, but not limited to, 0.1, 0.5, 0.75, etc. In some embodiments, the gel can be heated prior to the adding of the anode or cathode. In an illustrative embodiment, the anode chamber 115 and the cathode chamber 135 are made of a non-conductive material such as, but not limited to, e.g., a plastic, glass, wood, etc. When the gel anode 110 and the gel cathode 130 come into contact with one another and a gel electrolyte, the gel battery 100 is formed. Paths 170 and 175 illustrate physical paths that may be traversed by a portion of the gel anode 110 and a portion of the gel cathode 130, respectively, to create the gel battery 100. As discussed in further detail below, the paths 170 and 175 may be implemented as an anode dispensing channel mounted to the anode chamber 115 and a cathode dispensing channel mounted to the cathode chamber 135, respectively. In an illustrative embodiment, the gel electrolyte may be integrated into at least one of the gel anode 110 or the gel cathode 130 such that the gel battery can be formed.

As discussed in further detail below, a gel battery may be incorporated into or may form various types of food products, such as, but not limited to, snack foods, prepared foods, candies, and condiments. Specific examples of food products that the gel battery 100 may form include, but are not limited to, gel candy, a preserve, spreadable cheese, etc. Various food-grade products can be used for the gel anode 110, the gel cathode 130, and the gel electrolyte. For example, food-grade products that may make up the gel anode 110 include, but are not limited to, copper, carbon, manganese dioxide, or iron. The gel cathode 130 may be made of, but is not limited to, zinc or nickel. The gel electrolyte may be made of, but not limited to, phosphoric acid, ascorbic acid, and salt.

In one embodiment, the gel anode 110 and gel cathode 130 may be made of food-grade products such as vitamins and/or minerals. In some embodiments, the gel anode 110 and/or the gel cathode 130 can include an electrolyte. In another embodiment, a gel electrolyte can connect the gel anode 110 and the gel cathode 130. Upon ingestion of the gel battery by a subject, the vitamins and/or minerals can be delivered to the subject. The gel anode 110, the gel electrolyte and/or the gel cathode 130 may also be incorporated into a pill such as, but not limited to, a vitamin, a mineral, or a drug. In one such embodiment, the cathode chamber 135 and the anode chamber 115 may be formed by the pill or a digestible substance inserted into the pill and an electrolyte can be included in the gel anode 110 and/or the gel cathode 130.

Figure 2:
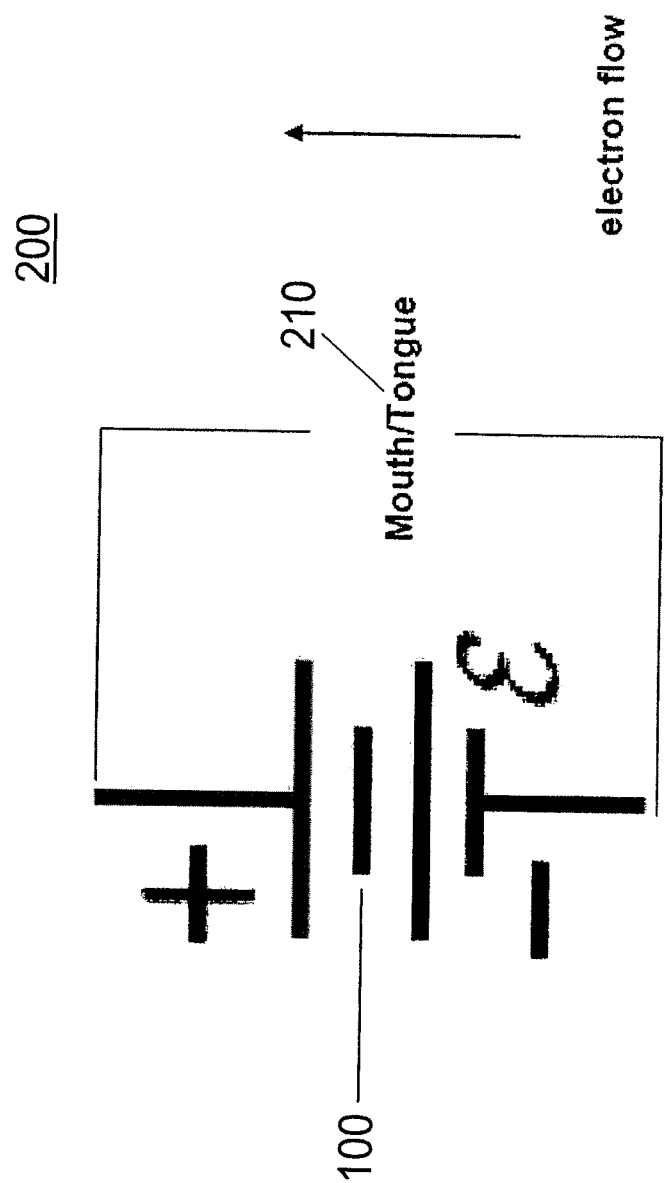
FIG. 2 illustrates an electrical circuit formed in a mouth with the gel battery in accordance with an illustrative embodiment.

FIG. 2 illustrates an electrical circuit 200 that includes a gel battery 100 and a mouth 210 in which the gel battery 100 is activated in accordance with an illustrative embodiment. For example, a tongue in the mouth 210 of a subject may connect the gel anode 110 and gel cathode 130 to form the circuit 200. The circuit 200, however, is not limited to being formed by a tongue. Rather, the circuit 200 may be formed with one or more other parts of the mouth, including, but not limited to, teeth, gums, the walls of the mouth, and/or any fluid that is associated with the mouth 210. Additionally, the circuit 200 is not limited to being formed in the mouth and can be formed on, but not limited to, skin or a scalp. Any conductive surface, such as, but not limited to, a counter top, a floor, a wall, etc. can also be used to connect the gel anode 110 and the gel cathode 130 to create the circuit 200. Once the circuit 200 is formed, the gel battery 100 generates a direct current that flows through the circuit 200. In an illustrative embodiment, the current is detectable by a user as a tingling of the parts of the mouth 210 or other body part that forms the circuit 200.

Figure 3:
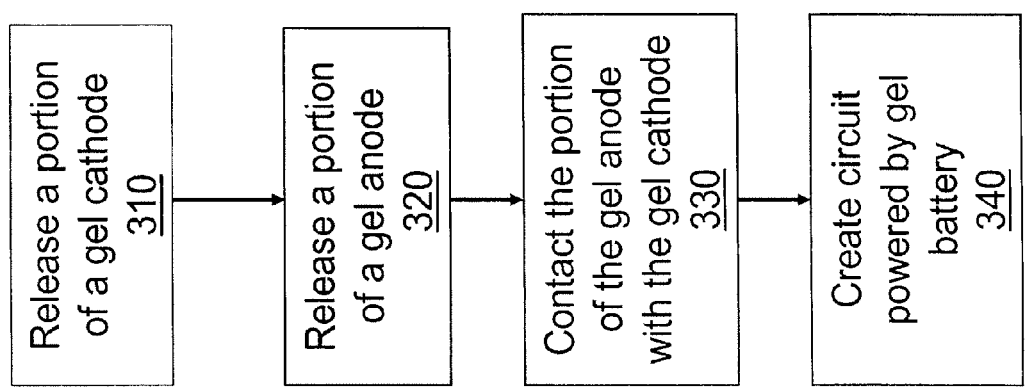
FIG. 3 is a flow diagram depicting operations performed in forming a gel battery in accordance with an illustrative embodiment.
Figure 4:
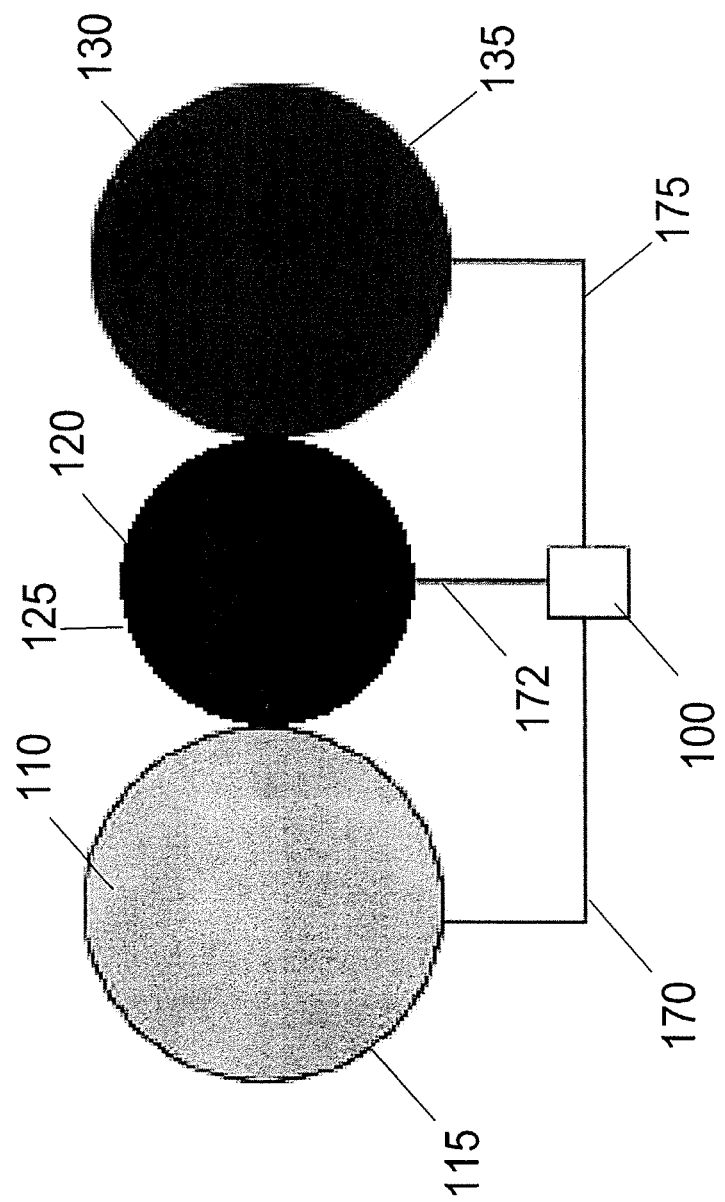
FIG. 4 illustrates a cathode chamber, an electrolyte chamber, and an anode chamber in accordance with an illustrative embodiment.

FIG. 3 is a flow diagram that depicts operations performed in creating a gel battery 100. Additional, fewer, and/or different operations may be performed depending on the particular implementation. In addition, one or more of the operations may be performed in a different order depending on the particular implementation. In an operation 310, a portion of the gel cathode 130, stored in a cathode chamber 135, is released. In an operation 320, a portion of the gel anode 110, stored in an anode chamber 115, is released. In an embodiment in which the cathode chamber 135 and the anode chamber 115 are part of a dispenser, the gel cathode 130 and the gel anode 115 may be released simultaneously as a user pushes a button (or other actuator) to activate the dispenser. The portion of the gel cathode 130 contacts the portion of the gel anode 110 to form a gel battery 100 that can generate an electrical current in an operation 330. In some embodiments, the gel anode 110 and/or the gel cathode 130 can include an electrolyte. In another embodiment, a gel electrolyte 120 is stored in a gel electrolyte chamber 125 (as shown in FIG. 4). In this embodiment, a portion of the gel electrolyte 120 can be released to connect the gel anode 110 and the gel cathode 130 to form a gel battery 100. In an operation 340, a circuit, such as, but not limited to, circuit 200 (of FIG. 2), is formed and electrical current flows through the circuit 200 powered by the gel battery 100.

FIG. 4 illustrates a cathode chamber 115, an electrolyte chamber 125, and an anode chamber 135 for forming the gel battery 100 in accordance with an illustrative embodiment. In one embodiment, the anode chamber 115, the electrolyte chamber 125, and the cathode chamber 135 can be incorporated into a dispenser for dispensing products such as, but not limited to, liquid soaps, deodorants, toothpastes, lotions, shampoos, cleaners, etc. In other embodiments, the chambers 115, 125, and 135 can be incorporated into a pill or into food products such as, but not limited to, gum, a jelly bean, candy, etc. The electrolyte chamber 125 can store a gel electrolyte 120. The gel anode 110 and/or the gel cathode 130 can also include an electrolyte, which may be different or the same as the electrolyte within the gel electrolyte 120. The gel electrolyte 120 can be made of various types of gels such as, but not limited to, aquagel, colloidal gel, hyrdogel, etc. In one embodiment, the gel electrolyte 120 can be made by adding an electrolyte such as, but not limited to, phosphoric acid, ascorbic acid, citric acid, or salt, to a gel. The electrolyte can be incorporated in the gel by stirring or using a homogenizer. In one embodiment, the volume concentration of the electrolyte is about 0.25. Other concentrations can also be used such as, but not limited to, 0.1, 0.5, 0.75, etc. In some embodiments, the gel can be heated prior to the adding of the electrolyte. An electrolyte can be added to the gel anode 110 and/or the gel cathode 130. In one embodiment, citric acid can be used as an electrolyte and can be added to the gel anode 110 and/or the gel cathode 130 in volume concentrations of, but not limited to, 0.01, 0.05, 0.1, 0.015, 0.25, etc.

In an alternative embodiment, the electrolyte chamber 125 can be a separator chamber that includes a separator such as, but not limited to, potato, starch, etc. The separator can be dispensed in between the gel anode 110 and the gel cathode 130 to separate the gel anode 110 from the gel cathode 130. In this embodiment, the gel anode 110 and/or the gel cathode 130 can include the gel electrolyte 120. In an illustrative embodiment, the separator can be porous to allow the flow of ions between the gel anode 110 and the gel cathode 130. In another embodiment, an electrolyte or the gel electrolyte 120 can be incorporated into the separator.

Path 172 illustrates a physical path that may be traversed by a portion of the gel electrolyte 120 such that the gel battery 100 can be formed. As discussed in further detail below, the path 172 may be implemented as an electrolyte dispensing channel mounted to the electrolyte chamber 125. In an illustrative embodiment, the gel battery 100 can be formed when at least a portion of the gel anode 110 comes into contact with at least a portion of the gel cathode 130, and when the gel electrolyte 120 comes into contact with at least the portion of the gel cathode 130 and/or at least the portion of the gel anode 110. As discussed in further detail below, the gel anode 110, the gel electrolyte 120, and gel cathode 130 can come into contact after being dispensed through an anode dispensing channel, an electrolyte dispensing channel, and a cathode dispensing channel, respectively.

FIG. 5A illustrates a cathode chamber 135 and an anode chamber 115 in accordance with an illustrative embodiment. In one embodiment, the anode chamber 115 and the cathode chamber 135 can be incorporated into a dispenser for dispensing products such as, but not limited to, deodorants, toothpastes, shampoos, liquid soaps, lotions, cleaners, antibacterial compositions, antiviral compositions, etc. In other embodiments, the chambers 115 and 135 can be incorporated into a pill or into food products such as, but not limited to, gum, a jelly bean, candy, etc. In these embodiments, the gel anode and/or the gel cathode can include an electrolyte. The anode chamber 115 and the cathode chamber 135 store a gel anode and gel cathode, respectively. The gel anode exits the anode chamber 115 through an anode dispensing channel 510. The gel cathode exits the cathode chamber 135 through a cathode dispensing channel 530. FIG. 5B illustrates a front plan view of the anode dispensing channel 510 and the cathode dispensing channel 530. The anode dispensing channel 510 is separated from the cathode dispensing chamber by a separator 540. As the gel anode 110 and gel cathode 130 exit their respective dispensing channels 510 and 530, the gel anode 110 and the gel cathode 130 come into contact with one another. A gel battery 100 is created when the gel anode and the gel cathode come into contact with one another.

An anode valve 545 can separate the anode chamber 115 from the anode dispensing channel 510. A cathode valve 550 can separate the cathode chamber 135 from the cathode dispensing channel 530. An actuator or button can cause the valves 545 and 550 to open or move such that the chambers 115 and 135 are placed in fluid communication with their respective channels 510 and 520. Open valves 545 and 550 can allow the gel anode and the gel cathode to be released from the chambers 115 and 135 into the chambers 510 and 530, respectively. In one embodiment, the gel anode contacts the gel cathode once dispensed from a dispenser. In this embodiment, the gel battery 100 is formed external to the dispenser.

In another embodiment, a combination channel is connected to the anode dispensing chamber 115 and the cathode dispensing chamber 135. The combination channel can allow the gel anode and the gel cathode to come into contact with one another prior to exiting the combination channel into an external environment. In these embodiments, the gel anode and/or the gel cathode can include an electrolyte.

FIG. 6A illustrates a cathode chamber 135, an electrolyte chamber 125, and an anode chamber 115 in accordance with an illustrative embodiment. The anode chamber 115 and the cathode chamber 135 store a gel anode and gel cathode, respectively. The electrolyte chamber 125 stores a gel electrolyte 120. The gel anode exits the anode chamber 115 through an anode dispensing channel 510. The gel electrolyte exits the electrolyte chamber 125 through an electrolyte dispensing chamber 520, and the gel cathode exits the cathode chamber 135 through a cathode dispensing channel 530. FIG. 6B illustrates a frontal plan view of the anode dispensing channel 510, electrolyte dispensing channel 520, and the cathode dispensing channel 530. As the gel anode, gel electrolyte, and gel cathode exit their respective dispensing channels 510, 520, and 530, the gel electrolyte comes into contact with both the gel anode and the gel cathode. A gel battery 100 is formed when the gel electrolyte comes into contact with the gel anode and the gel cathode.

An electrolyte valve 555 can separate the electrolyte chamber 125 from the electrolyte dispensing channel 520. An actuator or button can cause the valves 545, 555, and 550 to open or move such that the chambers 115, 125, and 135 are placed in fluid communication with their respective channels 510, 520, and 520. The gel electrolyte 120 can released from chamber 125 when valve 555 is open.

Figure 7:
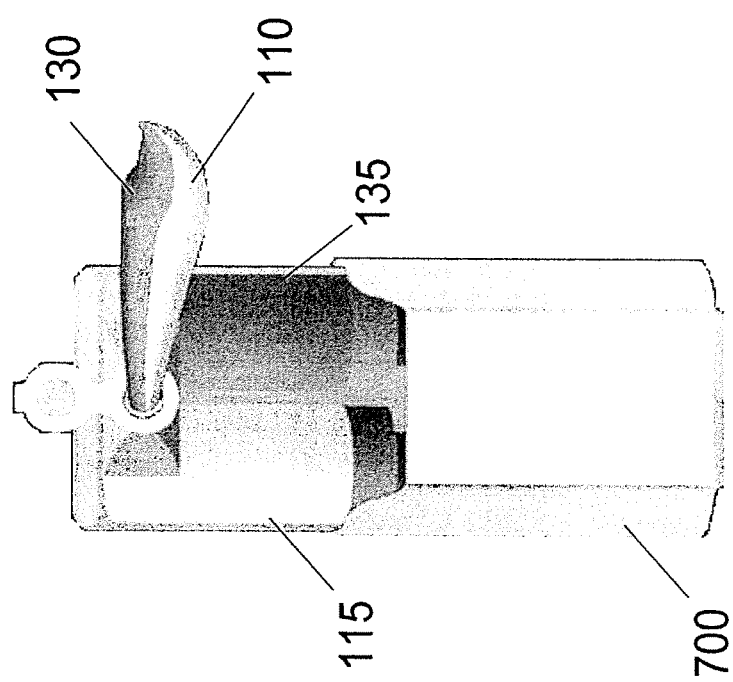
FIG. 7 illustrates a housing for a gel anode and a gel cathode in accordance with an illustrative embodiment.

FIG. 7 illustrates a gel battery dispenser 700 for forming a gel battery in accordance with an illustrative embodiment. The gel battery dispenser 700 includes the anode chamber 115 and the cathode chamber 135. FIG. 7 illustrates the dispensed gel cathode 130 being horizontally aligned with the dispensed gel anode 110. Any alignment, however, can be used, such as a vertical alignment. The gel battery dispenser 700 can include an actuator that when actuated causes a portion of the gel anode 110 to enter the anode dispensing chamber 510 and a portion of the gel cathode 130 to enter the cathode dispensing chamber 530. In one embodiment, a movable bottom of the dispenser or the anode chamber 115 and the cathode chamber 135 can cause the gel anode 110 and/or the gel cathode 130 to be dispensed. In another embodiment, the gel battery dispenser 700 also includes the electrolyte chamber 120, and the actuator allows a portion of the gel electrolyte 120 to enter the electrolyte dispensing chamber 520. In another embodiment, the gel battery dispenser 700 does not include an actuator, but instead the gel battery dispenser 700 can be a collapsible tube. Pressure applied to the gel battery dispenser 700 can cause an amount of the gel anode 110, gel cathode 130, and/or gel electrolyte 120 to exit the gel battery dispenser 700 and thereby form a gel battery 100. In another illustrative embodiment, the gel battery dispenser 700 can be disposable. For example, the gel battery dispenser 700 can be used to store a limited amount of the gel anode 110 and gel cathode 130, which in turn, can be used to create a limited number of gel batteries 100. The gel battery dispenser 700 can be opened, such as by tearing open a portion of the gel battery dispenser 700, and pressure applied to the gel battery dispenser 700 can be used to create the gel batteries 100.

In another embodiment, a pill can be used to store the gel anode 110, the gel cathode 130, and/or the gel electrolyte 120. The pill can include an anode chamber that is separated from a cathode chamber. A coating can surround the pill and encapsulate the anode chamber and the cathode chamber. The coating can be made of, but not limited to, e.g., gelatin, wax, hypromellose, methyl cellulose, hydroxypropyl cellulose, etc. In one embodiment, the pill can be swallowed by a subject and the coating can dissolve during digestion. Eventually, the gel anode and the gel cathode can be released from the pill and come into contact with one another to create a gel battery 100. In another embodiment, the pill can be chewed, which can release the gel anode 110 and the gel cathode 130. In some embodiments, an electrolyte can be included with the gel anode and/or the gel cathode. In other embodiments, the pill can include a separate electrolyte chamber. In another embodiment, the pill can also include a drug or vitamin, whose delivery is affected by the current generated by the gel formed battery 100. In another embodiment, one or more pills can be integrated into a component, such as, but not limited to, a preserve, a cheese product, a shampoo, or a cleaning agent. Pressure applied to the component, such as through spreading the component or massaging the component, can cause the coating to rupture and allow a portion of the gel anode can come into contact with a portion of the gel cathode to create a gel battery 100. In some embodiments, the gel anode and/or the gel cathode can include an electrolyte. In other embodiments, the pills can include an electrolyte chamber for storing a gel electrolyte. In yet another embodiment, a pill can contain only a portion of gel battery 100, such as the gel anode 110, the gel cathode 130, or the gel electrolyte 120. As the various pills rupture, components from different pills can be combined to form gel batteries. In one embodiment, spherical pills can be formed using sodium alginate fixed in a calcium chloride bath that can contain the gel anode 110, the gel electrolyte 120, or the gel cathode 130.

The current created by a gel battery 100 can be used in numerous ways. In one example, the current of a gel battery 100 can be used to effect delivery/absorption of a drug, to combat bacteria such as the bacteria that causes acne, to combat a virus such as the herpes virus, to stimulate muscles, etc. In addition, the current can also have an anti-bacterial effect and/or an anti-viral effect. In another embodiment, the gel anode 110, the gel electrolyte 120, or the gel cathode 130 can include an antibacterial agent. In an illustrative embodiment, the gel battery 100 can be a facial mask. The current from the gel battery 100 of the facial mask can be used as an acne treatment. The current from a gel battery 100 can also have an anti-viral effect and can be used in the treatment of skin sores or sores of the mouth, such as, but not limited to, canker sores. In another embodiment, the current from a gel battery 100 can be used to treat various skin conditions. In one illustrative embodiment, a gel battery 100 can be applied to a rash, an area of dry skin, and/or an area of irritated skin. The gel battery 100 can generate a current that flows through portions of the skin, which can be used to diminish itching in skin by providing a competing stimulus.

In another embodiment, the gel anode 110 and the gel cathode 130 can be made of cosmetic grade materials, such as, but not limited to, aluminum and carbon. In some embodiments, the gel electrolyte 120 can also be made of cosmetic grade materials. One or more gel batteries 100, using cosmetic grade materials, can be used as an antiperspirant and/or deodorant. For example, the gel anode 110 can include an aluminum complex and the gel cathode 130 can include carbon. In another embodiment, the gel battery 100 can include a cosmetic grade gel electrolyte 120 that contains salt. Illustrative aluminum complexes include, but are not limited to, aluminum chloride, aluminum chlorohydrate, and aluminum-zirconium compounds. The current produced by the gel battery 100 through a subject's skin can aid in the iontophoretic delivery of the aluminum-based complexes. Although not intending to be limited by theory, the aluminum-based complexes may aid in the formation of plugs in sweat glands, and thus, can help prevent perspiration. The aluminum-based complexes may also interact with keratin fibrils in sweat ducts and form a physical plug that prevents sweat from reaching the surface of skin. Accordingly, a gel battery 100 can be used to combat excessive sweating in an area of skin that is covered by the gel battery 100. One or more of the gel anode 110, the gel electrolyte 120, and the gel cathode 130 can also include fragrant materials.

In another illustrative embodiment, a gel battery 100 can be used to treat wounds or burns. The gel battery 100 can be applied to an affected portion of a subject's skin to provide a current through the subject's skin tissue. The current can be used to affect the healing of the wound through, but not limited to, increasing blood flow, enhancing tissue oxygenation, preventing an infection, stimulating epidermal cell reproduction, etc. In some embodiments, the electrical current can reduce the amount of scar tissue of a healed wound, resulting in a smoother and thinner scar.

In another illustrative embodiment, a gel battery 100 can include other components such that the gel battery 100 can be used as a mouthwash, as toothpaste, as shampoo, as an enhancement to hair dye, as a facial mask, as a teeth whitener, to deliver medicine such as, but not limited to, antacid medicine, cold medicine, nicotine, or anti-gas medicine, as an energy supplement, or for sexual stimulation. In each of these embodiments, a gel battery 100 can provide an electrical current that enhances the performance of the component for its intended purpose. For instance, the electrical current may facilitate the delivery of a drug contained within the gel anode 110, gel electrolyte 120, or gel cathode 130, or a drug that is taken simultaneously with the gel battery 100. In another embodiment, the current from the gel battery 100 may impede the flora of the mouth, and therefore, helps protect against cavities and/or gum disease. In addition, the gel battery 100 may also increase the production and secretion of saliva, which also helps protect against cavities and/or gum disease. In another embodiment, the gel battery 100 is a toothpaste that can include flavoring, such as, but not limited to, mint, bubble gum, berry, etc.

Another illustrative embodiment includes a gel battery 100 that includes a hair dye. As the hair dye is applied, the gel battery 100 can create an electrical current that flows through a person's scalp and hair. This electrical current can enhance the application of the hair dye, for example by reducing the application time and/or by increasing the absorption of the hair dye into hair. In another illustrative embodiment, a gel battery 100 includes a cleaner. Current from the gel battery 100 can help loosen dirt, grease, and/or enhance the cleaning ability of the cleaner.

The gel battery 100 can also be used for sexual stimulation. In an illustrative embodiment, one or more gel batteries 100 can be placed upon or within sex organs. The gel battery 100 can produce an electrical current that flows through a subject's genitals to provide sexual stimulation. In another embodiment, the gel anode 110 can be placed one subject's body and the gel cathode 130 can be placed on a second subject's body. When the gel anode 110 and the gel cathode 130 come into contact a gel battery 100 is created, and an electrical current will flow between the subjects. In these embodiments, the gel anode 110 and/or the gel cathode 130 can include an electrolyte. In addition, the effects of the gel battery 100 are transferable from one person to another. For instance, portions of a gel battery 100 can be transferred between two individuals through kissing, fellatio, cunnilingus, sexual intercourse, etc. The electrical current can result in heightened sexual stimulation.

A number of parameters may influence the properties of the gel battery 100. For example, the terminal voltage of the gel battery 100, the amperage of the circuit 200 (FIG. 2), and the lifespan of the gel battery 100 may be configured based upon the properties of the gel battery 100. The materials that make up the gel anode 110 and gel cathode 130 provide properties that affect the voltage of the gel battery 100. In one embodiment, the amperage of the circuit 200 can be increased by increasing the molar concentration of the electrolyte in the gel cathode 130 and/or gel anode 110. Increasing the surface area between the gel anode 110, gel cathode 130, and/or the gel electrolyte 120 can also increase the amperage of the circuit 200. In one embodiment, the surface area is increased based upon the shapes of the gel anode 110 and the gel cathode 130 prior to coming into contact with one another. The shapes can be formed based on the shape of the apertures through which the gel anode 110 and gel cathode 130 are dispensed (or extruded). The placement of the apertures relative to one another can also be used to increase amount of surface area of the connection between the gel anode 110 and the gel cathode 130.

In one embodiment, the gel anode 110 can be, but is not limited to, a hexagon, a pentagon, a triangle, etc. Any corresponding shape that increases the surface area of the connection of the gel anode 110 and gel cathode 130 can be used. The gel cathode 130 can be a shape that comes into contact with multiple sides of the gel anode 110. As an example, the gel anode 110 may be dispensed in the shape of a triangle and the gel cathode 130 may be dispensed in a "V" shape that corresponds to an apex and two sides of the triangle. The aperture that dispenses the gel cathode 130 can be positioned relative to the aperture that dispenses the gel anode 110 such that the "V" shaped gel cathode 130 comes into contact with two sides of the triangular shaped gel anode 110. Alternatively, the gel cathode 130 can be shaped as, but not limited to, a hexagon, a triangle, a pentagon, a rectangle, an octagon, etc, and the aperture that dispenses the gel anode 110 can be shaped and positioned such that the gel anode 110 comes into contact with multiple sides of the gel cathode 130. For example, an aperture that dispenses the gel cathode 130 can be a hexagon, and an aperture that dispenses the gel anode 110 can be shaped and positioned such that gel anode 110 comes into contact with two, three, four, etc. sides of the hexagonally shaped gel cathode 130.

The size of the gel battery 100 is another property that may be used to configure the gel battery 100. Specifically, the size of the gel battery 100 may be used to configure how long the gel battery 100 is operable. Generally, the more gel anode 110 and gel cathode 130 used to create the gel battery 100 the longer the battery will remain active. The concentration of the anode, cathode, and electrolyte also impacts the longevity of the gel battery 100. For example, higher concentrations of the anode, cathode, and electrolyte within a gel results in a longer lasting gel battery 100. A gel battery 100 may remain active between 5 and 60 seconds. In alternative embodiments, the gel battery 100 can be configured to remain active for less than 5 seconds or greater than 60 seconds. The time the gel battery 100 is active may be increased by using a greater amount and/or concentration of gel anodes 110 and gel cathodes 130. The amount and/or concentration of the gel electrolyte 120 or the concentration of an electrolyte in the gel anode 110 and/or gel cathode 130 also impacts the activation length of the gel battery 100. Larger amounts or larger concentrations of the gel electrolyte 120 and higher concentrations of an electrolyte in the gel anode 110 and/or the gel cathode 130 can increase the time the gel battery 100 remains active.

Figure 8:
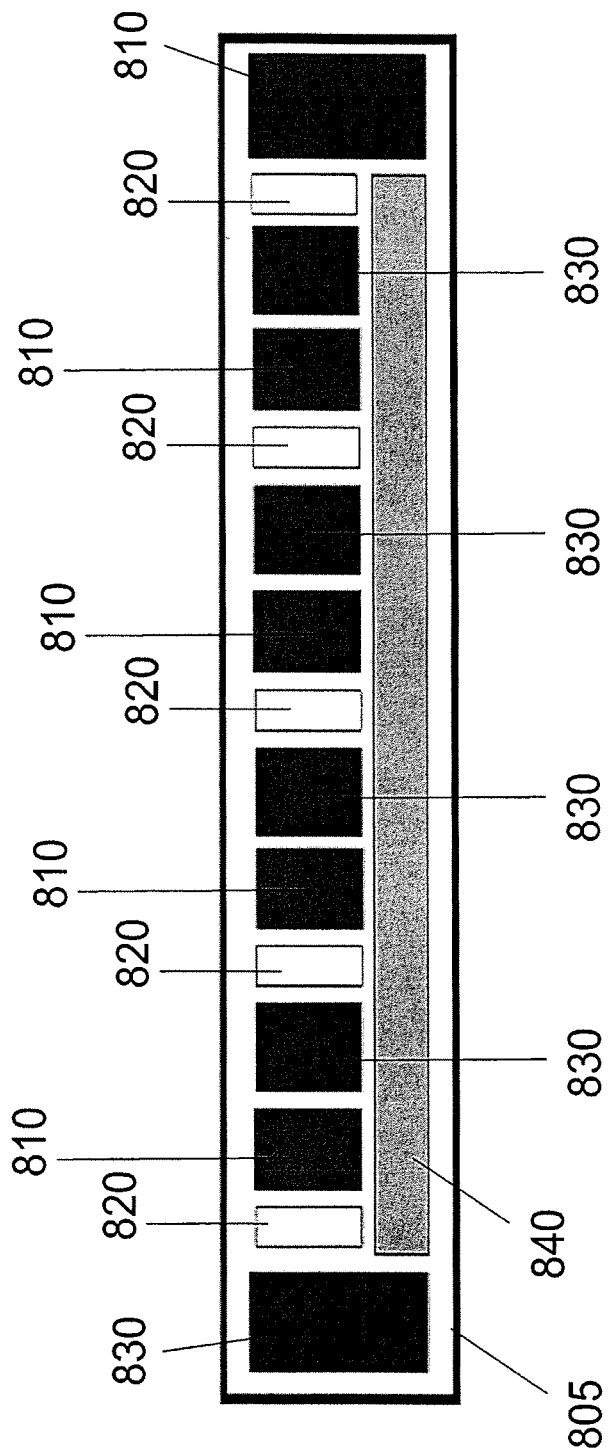
FIG. 8 illustrates multiple gel batteries in series in accordance with an illustrative embodiment.

The terminal voltage of the battery 100, the current of the circuit 200, and lifespan of the battery 100 may be also be controlled by using multiple batteries. FIG. 8 illustrates multiple gel batteries in series in accordance with an illustrative embodiment. A manifold dispensing nozzle 805 can be used to create multiple gel batteries in series with one another. In one embodiment, the manifold dispensing nozzle can be created using three dimensional printing. An anode manifold can be connected to the anode storage chamber 115. The anode manifold can dispense any number of portions 810 of the gel anode 110. A cathode manifold can connect to the cathode chamber 135 and dispense a number of portions 830 of the gel cathode 130. Similarly in another embodiment, an electrolyte manifold can connect to electrolyte chamber 125 and dispense numerous portions 820 of the gel electrolyte 120. The portions 810 of the gel anode 110 and the portions 830 of the gel cathode 130 can be interleaved with one another to create a number of gel batteries that are in series with one another. In another embodiment, the multiple gel batteries can be connected in parallel with one another. For ease of illustration, the various illustrated portions 810, 820, and 830 have space between them. These portions, however, can be connected to form the multiple gel batteries in series with one another. A payload 840 can be included along with the batteries. The payload can be, but is not limited to, a food, a lotion, a toothpaste, a cleaner, a shampoo, a hair dye, a facial mask, a medicine, a pharmaceutical composition, or a teeth whitener.

Numerous embodiments of the gel battery 100 can be incorporated into various foods. In addition to producing a current, a gel battery 100 can increase the amount of saliva generated in the mouth of a user. Saliva can be produced by the stimulation of either or both the sympathetic nervous system and the parasympathetic nervous system. For example, stimulation of the trigeminal nerve can result in an increase in the secretion and production of saliva. While not intending to be limited by theory, a gel battery 100 may stimulate the trigeminal nerve and/or other nerves of the sympathetic and parasympathetic nervous systems. Accordingly, a gel battery 100 can result in an increase in both saliva production and saliva secretion. In an illustrative embodiment, a gel battery can be a gel mouth rinse or toothpaste. The gel battery 100 can increase the saliva production and saliva secretion of the user by stimulating the sympathetic nervous system and/or parasympathetic nervous system. Accordingly, a gel battery 100 can be used to treat such conditions as Xerostomia (e.g., dry mouth) by increasing saliva production and secretion. The current generated by the gel battery 100 can enhance the absorption of a drug contained within the gel anode 110, gel electrolyte 120, and/or gel cathode 130 through stimulation of tissues in the mouth, stomach, and/or small intestines.

EXAMPLES

The present compositions and methods will be understood more readily by reference to the following examples, which are provided by way of illustration and are not intended to be limiting in any way.

Example 1

Treatment of Dry Mouth

A gel battery can be used as a treatment of dry mouth. A housing can include a gel anode chamber, a gel cathode chamber, and a gel electrolyte chamber. Alternatively, the electrolyte may be incorporated into one or both of the gel anode or the gel cathode. Pressing on an actuator of the housing can release a portion of the gel anode, a portion of the gel cathode, and a portion of the gel electrolyte that come into contact with one another upon exiting the housing to create the gel battery. The gel battery can be administered orally to increase saliva production and secretion levels compared to the levels prior to the creation and administration of the gel battery. The gel battery, therefore, will be useful in treating dry mouth. In one embodiment, the gel battery may be incorporated into a food product such as a candy, a preserve, a cheese, etc. and used to treat dry mouth upon ingestion of the food product.

Example 2

Antiperspirant

A gel anode includes cosmetic grade aluminum and a gel cathode includes cosmetic grade carbon. The gel anode also includes sodium chloride that acts as an electrolyte. The gel anode and the gel cathode or stored in an anode chamber and a cathode chamber, respectively. Both of the chambers are housed in a gel antiperspirant container. The container includes an actuator that forces a portion of the anode and the gel cathode through a top of the container. Applying the gel anode and the gel cathode to an underarm causes a portion of the gel anode and the gel cathode to come into contact to create a gel battery. The gel battery results in current flowing through the underarm and results in a reduction in the amount of sweat produced by a subject compared to the amount of sweat produced prior to the application of the gel battery. The aluminum-based complexes may aid in the formation of plugs in sweat glands, and thus, can help prevent perspiration. The aluminum-based complexes may also interact with keratin fibrils in sweat ducts and form a physical plug that prevents sweat from reaching the surface of skin.

Example 3

Lotion

A collapsible tube includes a manifold dispensing nozzle that creates multiple gel batteries in series with one another. The manifold dispensing nozzle is created using three dimensional printing. The manifold dispensing nozzle can include an anode manifold that is in fluid communication with the anode chamber. The manifold dispensing nozzle can also include a cathode manifold and an electrolyte manifold that are in fluid communication with the cathode chamber and the electrolyte chamber, respectively. The anode, electrolyte, and the cathode manifolds can interleave portions of the gel anode, the gel electrolyte, and the gel cathode together to form two or more gel batteries in series with one another. In another embodiment, the manifold dispensing nozzle can include an anode dispensing channel and a cathode dispensing channel. In this embodiment, the gel anode and/or the gel cathode can include an electrolyte. In another embodiment, the manifold dispensing nozzle can include an anode dispensing channel, an electrolyte dispensing channel, and a cathode dispensing channel.

The manifold dispensing channel can also dispense a payload, such as a lotion. In one embodiment, the payload is between a gel anode and a gel cathode that contacts a subject's skin. In this embodiment, one ore more batteries may be dispensed between the gel anode and the gel cathode that contacts the subject's skin. In another embodiment, the one or more batteries between the gel anode and the gel cathode that contact the skin of a subject are sandwiched between two layers of the payload. This allows the subject to apply the payload without concern regarding the orientation of the payload and the gel batteries.

Example 4

Shampoo

A dispenser can include an anode chamber and a cathode chamber. The gel anode and/or the gel cathode includes an electrolyte. Additionally, the gel anode and/or the gel cathode includes a shampoo. The gel anode and the gel cathode are dispensed from the dispenser and combined upon being dispensed. Portions of the gel anode and gel cathode continue to be connected as the shampoo is massaged into a subject's hair to form one or more gel batteries. Electrical current from the gel batteries flow through the subject's hair and scalp and help the shampoo remove oil, dirt, dandruff, contaminants, etc from the subject's hair. Such stimulation will also have the beneficial effective of providing stimulation and a pleasant sensation to a subject's scalp and other body areas.

Example 5

Muscle Stimulation

A gel battery can be formed by dispensing a portion of a gel anode and a gel cathode. The gel anode and/or the gel cathode include an electrolyte. In another embodiment, a portion of a gel electrolyte is dispensed with the gel anode and the gel cathode. The gel anode, the electrolyte, and the gel cathode are connected and form a gel battery. The gel battery can be applied to an area of a subject's skin, e.g., under or around the eye or mouth, hands, arms, stomach, etc. Electrical current generated by the gel battery flows across the subject's skin and causes the subject's muscles local to the placement of the gel battery to be stimulated.

Example 6

Toothpaste

A gel battery can be formed in conjunction with dispensing an amount of toothpaste. A dispenser dispenses a portion of a gel anode, a portion of a gel electrolyte, and a portion of the gel cathode. In another embodiment, the gel anode and/or the gel cathode can include the gel electrolyte. The gel anode, gel electrolyte, and/or the gel cathode include toothpaste components, such as, but not limited to, abrasives, fluoride, detergents, whiteners, etc. Upon being dispensed or immediately prior to being dispensed, the portion of the gel anode, the portion of the gel electrolyte, and the portion of the gel cathode connect and form a gel battery. Applying the toothpaste to a subject's mouth results in a current that flows various portions of a subject's mouth, such as but not limited to, gums, teeth, tongue, etc. The electrical current can help the clean the subject's teeth, whiten the subject's teeth, combat against gum disease, freshen the subject's breath, etc.

Example 7

Face Cream

A gel battery can be formed by dispensing a portion of a gel anode and a gel cathode. The gel anode and/or the gel cathode can include an electrolyte. In another embodiment, a portion of a gel electrolyte is dispensed with the gel anode and the gel cathode. The gel anode, the electrolyte, and the gel cathode are connected and form a gel battery. One or more of the gel anode, gel cathode, or gel electrolyte can include components of a face cream, such as, but not limited to, a lotion, a fragrance, bleaching agent, hair dye, moisturizer, hair removal component, etc. The face cream can be applied to a subject's a face and can be used for, but not limited to, stimulating a muscle, bleaching facial hair, moisturizing, etc. Current can be generated by the gel battery to affect or enhance the use of the face cream by stimulating a muscle, increasing the absorption of the hair dye, enhancing the moisturizing agent, etc.

One or more flow diagrams have been used herein. The use of flow diagrams is not meant to be limiting with respect to the order of operations performed. The herein-described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Specific examples of "operably couplable" include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended, hereto and their equivalents.

What is claimed is:

1. An apparatus comprising:
   a cathode chamber configured to store a gel cathode;
   an anode chamber configured to store a gel anode;
   a cathode dispensing channel in fluid communication with the cathode chamber and configured to dispense at least a portion of the gel cathode; and
   an anode dispensing channel in fluid communication with the anode chamber and configured to dispense at least a portion of the gel anode, wherein at least the portion of the gel cathode and at least the portion of the gel anode are configured to come into contact upon exiting the cathode dispensing channel and the anode dispensing channel, respectively, to form an active battery that is configured to generate an electrical current.

2. The apparatus of claim 1, wherein the gel anode comprises a food grade gel anode, and wherein the gel cathode comprises a food grade gel cathode.

3. The apparatus of claim 2, wherein the food grade gel anode comprises at least one of copper, carbon, manganese dioxide, or iron.

4. The apparatus of claim 2, wherein the food grade gel cathode comprises at least one of zinc or nickel.

5. The apparatus of claim 2, wherein at least one of the food grade gel anode and the food grade gel cathode includes a vitamin that is configured to be administered via the active battery.

6. The apparatus of claim 1, further comprising a combination chamber in fluid communication with the cathode dispensing channel, the anode dispensing channel, and an external environment, wherein the active battery is formed in the combination chamber.

7. The apparatus of claim 1, wherein the cathode dispensing channel and the anode dispensing channel are in fluid communication with an external environment, and wherein the active battery is formed in the external environment.

8. The apparatus of claim 1, wherein at least one of the gel anode and the gel cathode includes an electrolyte.

9. The apparatus of claim 8, wherein the electrolyte comprises at least one of phosphoric acid, ascorbic acid, or salt.

10. The apparatus of claim 1, further comprising an actuator operatively coupled to the cathode chamber and the anode chamber, the actuator configured to cause at least the portion of the gel cathode to enter the cathode dispensing channel and at least the portion of the gel anode to enter the anode dispensing channel.

11. The apparatus of claim 1, further comprising:
    an electrolyte chamber configured to store a gel electrolyte; and
    an electrolyte dispensing channel in fluid communication with the electrolyte chamber and configured to dispense at least a portion of the gel electrolyte, wherein at least the portion of the gel electrolyte comes into contact with at least the portion of the gel cathode and at least the portion of the gel anode to form the active battery.

12. The apparatus of claim 1, wherein the active battery is configured to increase production of saliva.

13. The apparatus of claim 1, wherein the active battery comprises a mouthwash gel.

14. The apparatus of claim 1, wherein the electrical current is configured to reduce flora within a mouth.

15. The apparatus of claim 1, wherein the electrical current is configured to combat gum disease.

16. The apparatus of claim 1, further comprising a separator that is configured to separate the cathode dispensing channel from the anode dispensing channel.

17. The apparatus of claim 1, further comprising:
an anode manifold that is in fluid communication with the anode dispensing channel configured to dispense a plurality of portions of the gel anode; and
a cathode manifold that is in fluid communication with the cathode dispensing channel configured to dispense a plurality of portions of the gel cathode, wherein the plurality of portions of the gel anode are interleaved with the plurality of portions of the gel cathode to form a plurality of actives batteries in series or parallel with one another.

18. A method comprising:
releasing at least a portion of a gel cathode from a cathode chamber of a dispenser, wherein the gel cathode is stored in the cathode chamber;
releasing at least a portion of a gel anode from an anode chamber of the dispenser, wherein the gel anode is stored in the anode chamber; and
causing at least the portion of the gel cathode to contact at least the portion of the gel anode to form an active battery that is configured to generate an electrical current.

19. The method of claim 18, further comprising administering the active battery in a mouth of a subject to treat dry mouth.

20. The method of claim 18, wherein at least one of the gel anode and the gel cathode includes an electrolyte.

21. The method of claim 18, wherein at least the portion of the gel cathode and at least the portion of the gel anode are released in response to activation of an actuator on the dispenser.

22. The method of claim 18, further comprising:
releasing at least a portion of an electrolyte from an electrolyte chamber of the dispenser; and
causing at least the portion of the gel electrolyte to contact at least the portion of the gel cathode and at least the portion of the gel anode to form the active battery.

23. The method of claim 18, further comprising administering the active battery to reduce flora within a mouth.

24. The method of claim 18, further comprising using the electrical current to combat gum disease in a subject.

25. An apparatus comprising:
means for storing a gel cathode;
means for storing a gel anode; and
means for causing at least a portion of the gel cathode to contact at least a portion of the gel anode to form an active battery that is configured to generate an electrical current.

26. An apparatus comprising:
a cathode chamber configured to store a gel cathode;
an anode chamber configured to store a gel anode; and
a receptacle configured to house the cathode chamber and the anode chamber, wherein the receptacle is configured to open allowing at least a portion of the gel cathode and at least a portion of the gel anode to come into contact upon exiting the receptacle to form an active battery that is configured to generate an electrical current.

* * * * *

UNITED STATES PATENT AND TRADEMARK OFFICE
CERTIFICATE OF CORRECTION

PATENT NO.          : 8,744,593 B2
APPLICATION NO.     : 13/392424
DATED               : June 3, 2014
INVENTOR(S)         : Godden It is certified that error appears in the above-identified patent and that said Letters Patent is hereby corrected as shown below:

On the Title Page

On Page 2, in item (56), under "OTHER PUBLICATIONS", in Column 2, Line 6, delete "Applicatgion" and insert -- Application --, therefor.

On Page 2, in item (56), under "OTHER PUBLICATIONS", in Column 2, Line 30, delete "Appin." and insert -- Appln. --, therefor.

In the Specification

In Column 6, Line 15, delete "chamber 115," and insert -- chamber 135, --, therefor.

In Column 6, Line 16, delete "chamber 135" and insert -- chamber 115 --, therefor.

In Column 8, Lines 2-3, delete "channels 510, 520, and 520." and insert -- channels 510, 520, and 530. --, therefor.

In Column 8, Line 20, delete "chamber 120," and insert -- chamber 125, --, therefor.

In Column 12, Line 66, delete "the anode" and insert -- the gel anode --, therefor.

In Column 13, Line 40, delete "one ore" and insert -- one or --, therefor.

In Column 15, Line 22, delete "the an" and insert -- the art --, therefor.

In Column 16, Line 13, delete "appended," and insert -- appended --, therefor.

Signed and Sealed this
Twenty-first Day of October, 2014

Michelle K. Lee
*Deputy Director of the United States Patent and Trademark Office*